US00PP11719P

United States Patent [19]

Fischer

[11] Patent Number: Plant 11,719

[45] Date of Patent: Dec. 26, 2000

[54] APPLE TREE NAMED 'PI 80 SELECT'

[76] Inventor: Manfred Fischer, Genbank Obst Dresden-Pillnitz am Institut für Pflanzengenetik und Kulturpflanzenforschung Gatersleben, D-01326 Dresden, Germany

[21] Appl. No.: 08/869,069

[22] Filed: Jun. 4, 1997

[51] Int. Cl.[7] ..... A01H 5/00

[52] U.S. Cl. ..... Plt./174

[58] Field of Search ..... Plt./34.1, 174, Plt./161, 175

*Primary Examiner*—Howard J. Locker

*Attorney, Agent, or Firm*—Klarquist Sparkman Campbell Leigh & Whinston LLP

[57] ABSTRACT

A new and distinct variety of apple rootstock named 'Pi 80 Select' characterized by (1) dwarfing when used as a rootstock; (2) excellent compatibility with a number of different apple cultivars; (3) good propagability; (4) sufficient mechanical strength for vigorous scion varieties; and (5) strong rooting capacity.

5 Drawing Sheets

BACKGROUND OF THE INVENTION

The present invention comprises a new and distinct variety of apple tree (*Malus pumila mill*), referred to by the varietal name 'Pi 80 Select'.

The 'Pi 80' variety is the result of a cross of 'M9' and 'M4'. The original plant of the 'Pi 80 select' variety is the result of a mutation of the 'Pi 80' variety. The 'Pi 80 select' variety was originally asexually propagated using the stoolbed layering method in Dresden Germany.

The 'Pi 80 Select' variety is believed to be a naturally occurring mutation of 'Pi 80'. 'Pi 80 Select' has not been observed under all possible environmental conditions. The phenotype may vary significantly with variations in environment such as temperature, light intensity, and daylength, without any variation in genotype. However, the following combination of traits have been repeatedly observed in asexually propagated progeny of the 'Pi 80 Select' variety and are determined to be the basic characteristics of this variety and distinguish this variety as a new and distinct variety of apple tree: (1) dwarfing when used as a rootstock; (2) excellent compatibility with a number of different apple cultivars; (3) good propagability; (4) sufficient mechanical strength for vigorous scion varieties; and (5) excellent rooting characteristics. The new variety is readily identified by the uniformity of these characteristics.

Asexual reproduction through succeeding generations shows that these characteristics are extablished and transmitted through succeeding asexual propagations.

DETAILED DESCRIPTION

The following is a detailed description of the 'Pi 80 Select' variety based on plants produced and observed under orchard conditions at the Genbank Obst Dresden-Pillnitz at the Institut für Pflanzengenetik und Kulturpflanzenforschung Gatersleben, Germany and in McMinnville, Oreg.

Color references are made in accordance with The Royal Horticultural Society (R.H.S.) standards, except where general color terms of ordinary dictionary significance is obvious.

In order to improve the stoolbed and fruit-growing characteristics of European apple rootstocks by breeding and clonal selection, the cross 'M 9'×'M 4' (pollen parent) was performed, resulting in a population of seedlings. The best seedlings were cloned (vegetatively propagated) and tested in the stoolbed for compatibility with various apple cultivars, including Laxtons Superb, Berlepsch, and Boskoop. Later, the clones were tested in the field for pomological performance and compatibility with Alkmene, Auralia, Carola, Golden Delicious, James Grieve, Jonathan, and Ontario. Pomological testing was preformed under a minimal pruning regime.

Of these clones, 'Pi 80' was selected and asexually propagated. 'Pi 80' does not have excellent rooting properties. I selected 'Pi 80 Select' as a better layering plant than 'Pi 80', and 'Pi 80 Select' was asexually propagated under my direction and control. 'Pi 80 Select' is a dwarfing rootstock suitable for intensive to semi-intensive planting systems and displays a number of advantages over other apple rootstocks as discussed below.

Figure 1:
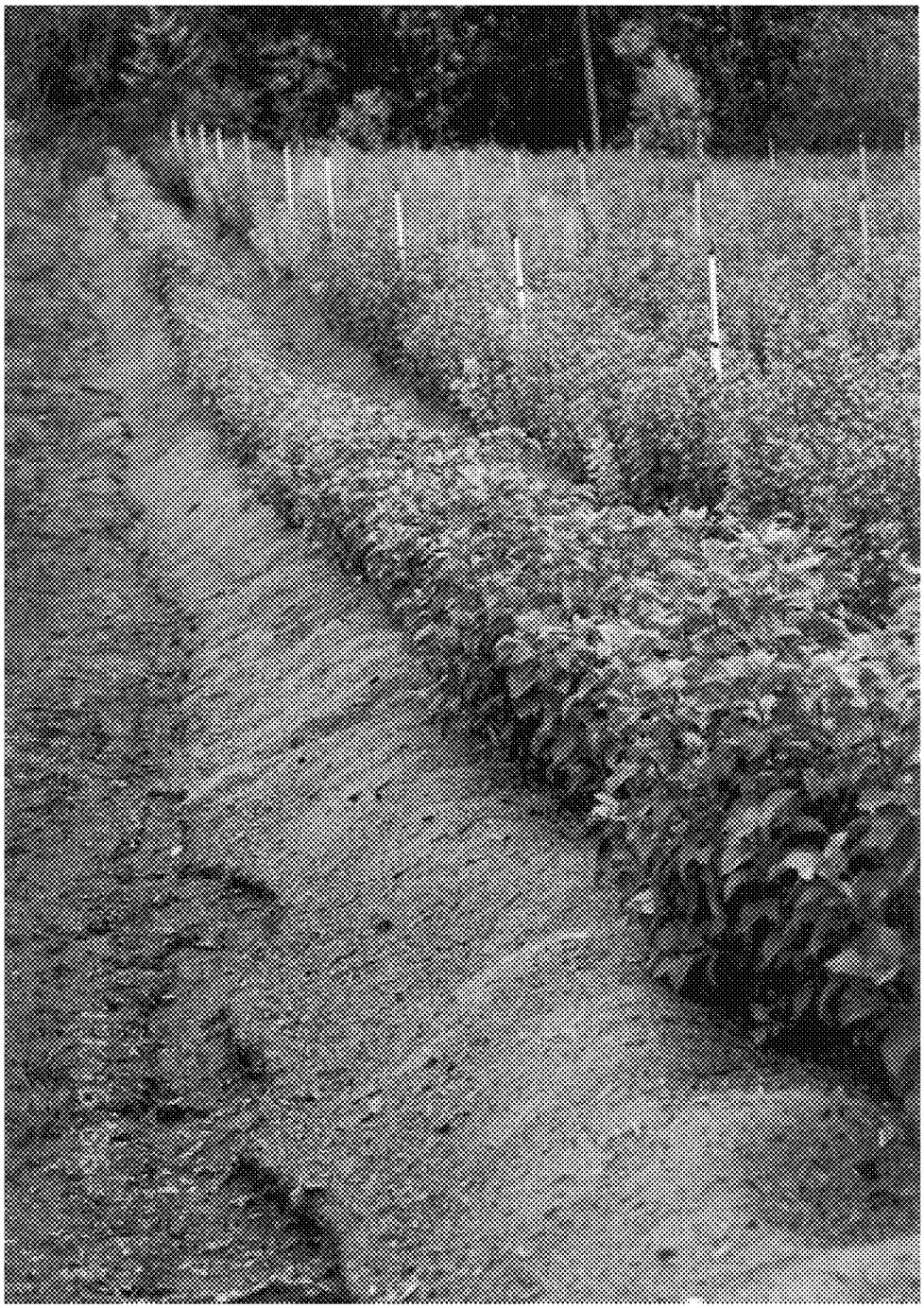
FIG. 1 is a view of a row of trees of 'Pi 80 Select'.
Figure 2:
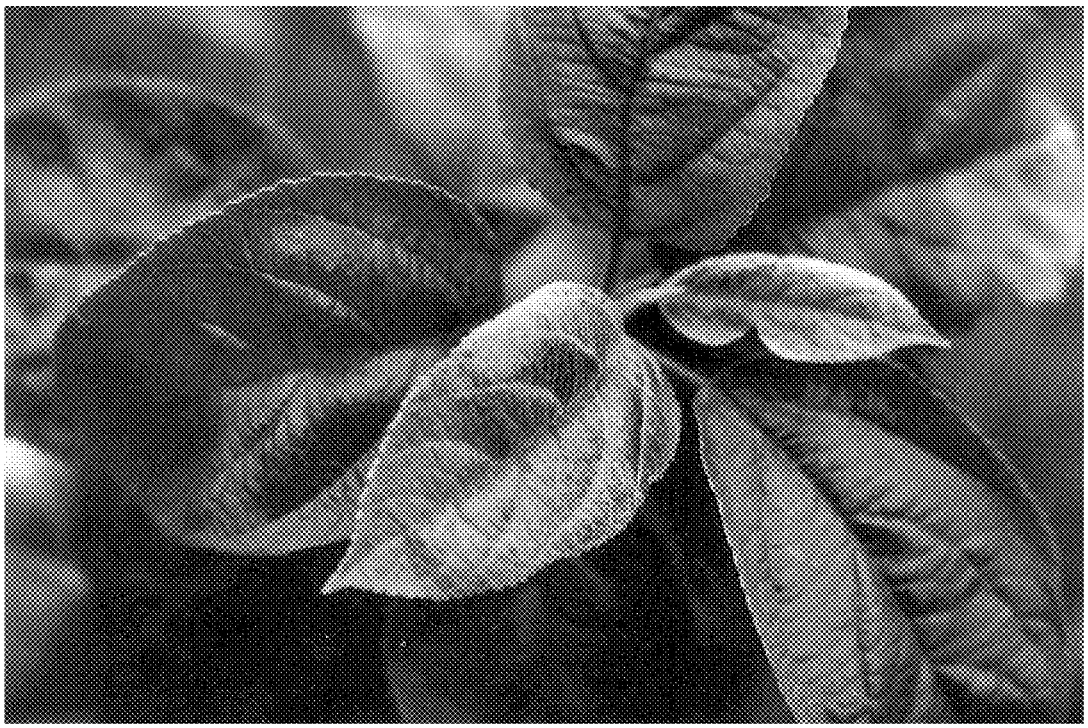
FIG. 2 is a view of a typical twig and leaves of 'Pi 80 Select'.
Figure 3:
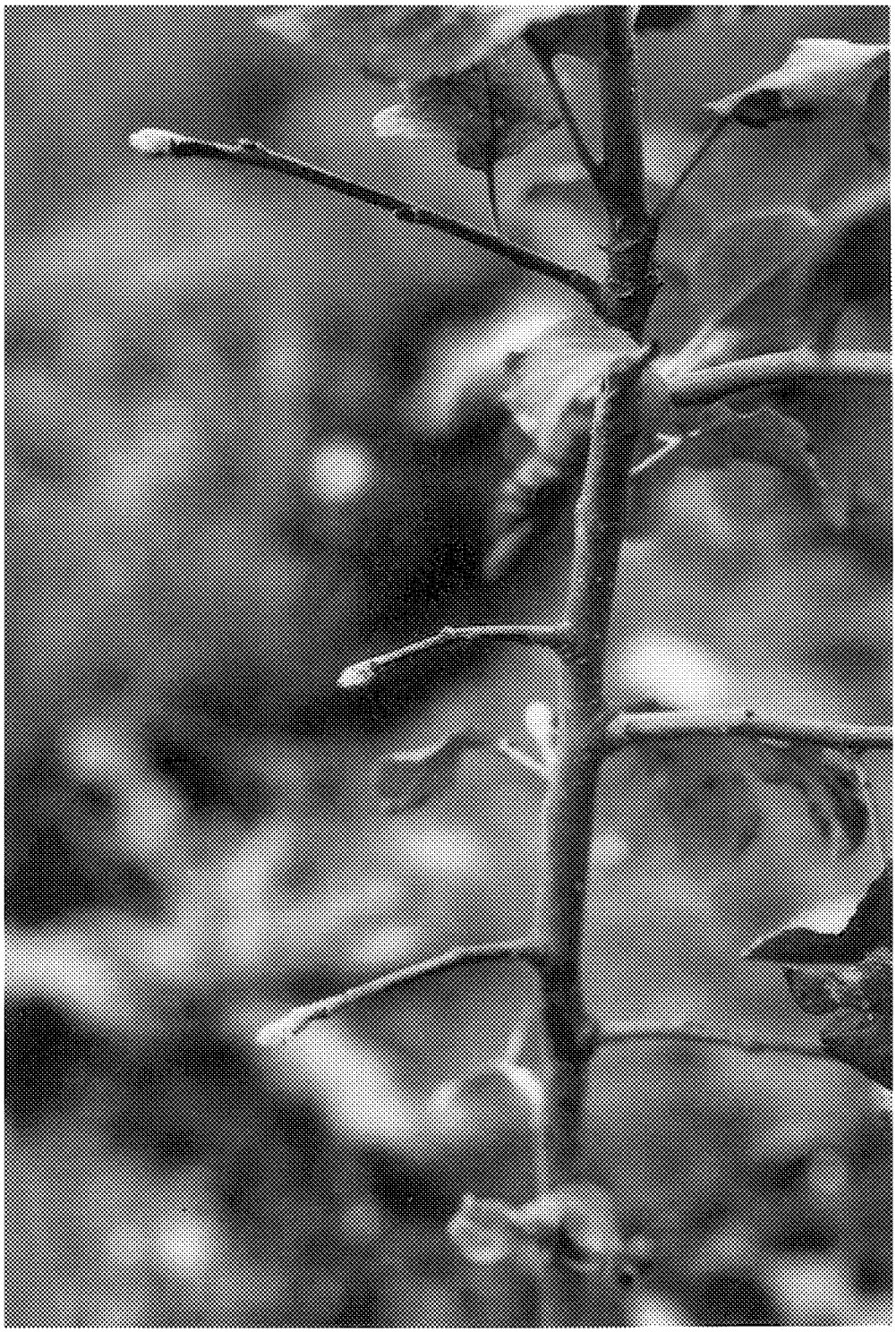
FIG. 3 is a view of a branch of 'Pi 80 Select'.
Figure 4:
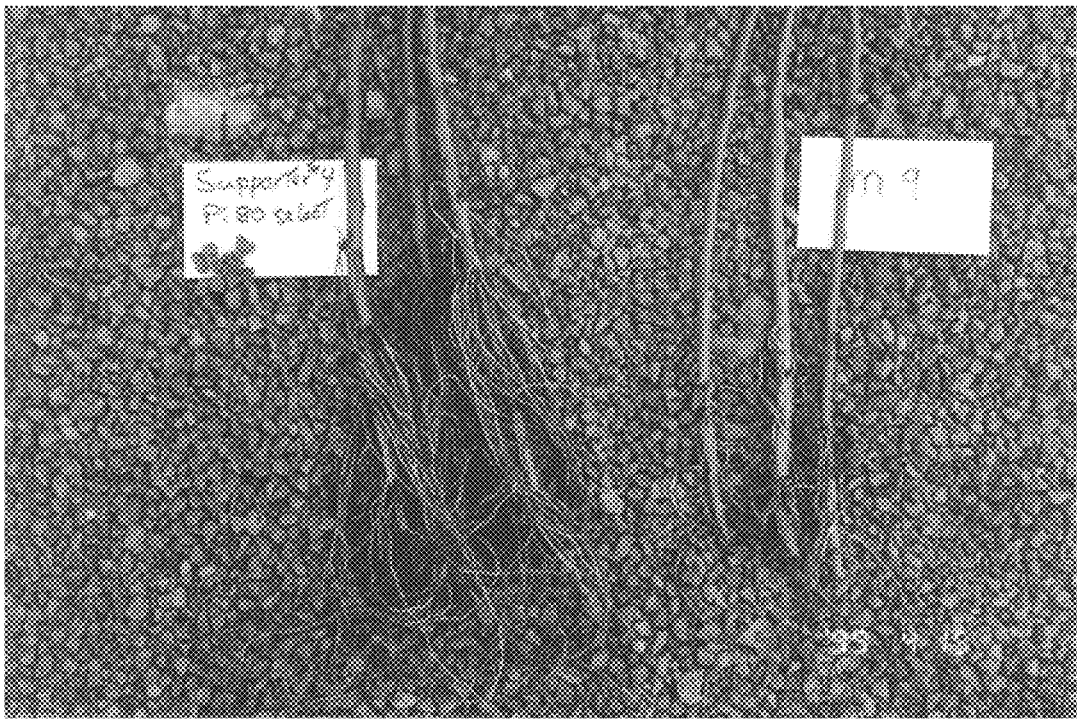
FIG. 4 is a view of roots of plants of the 'Pi 80 Select' variety in comparison to roots of plants of the 'M9' variety obtained by layering and which were grown under similar growing conditions at a nursery in McMinnville, Oreg.
Figure 5:
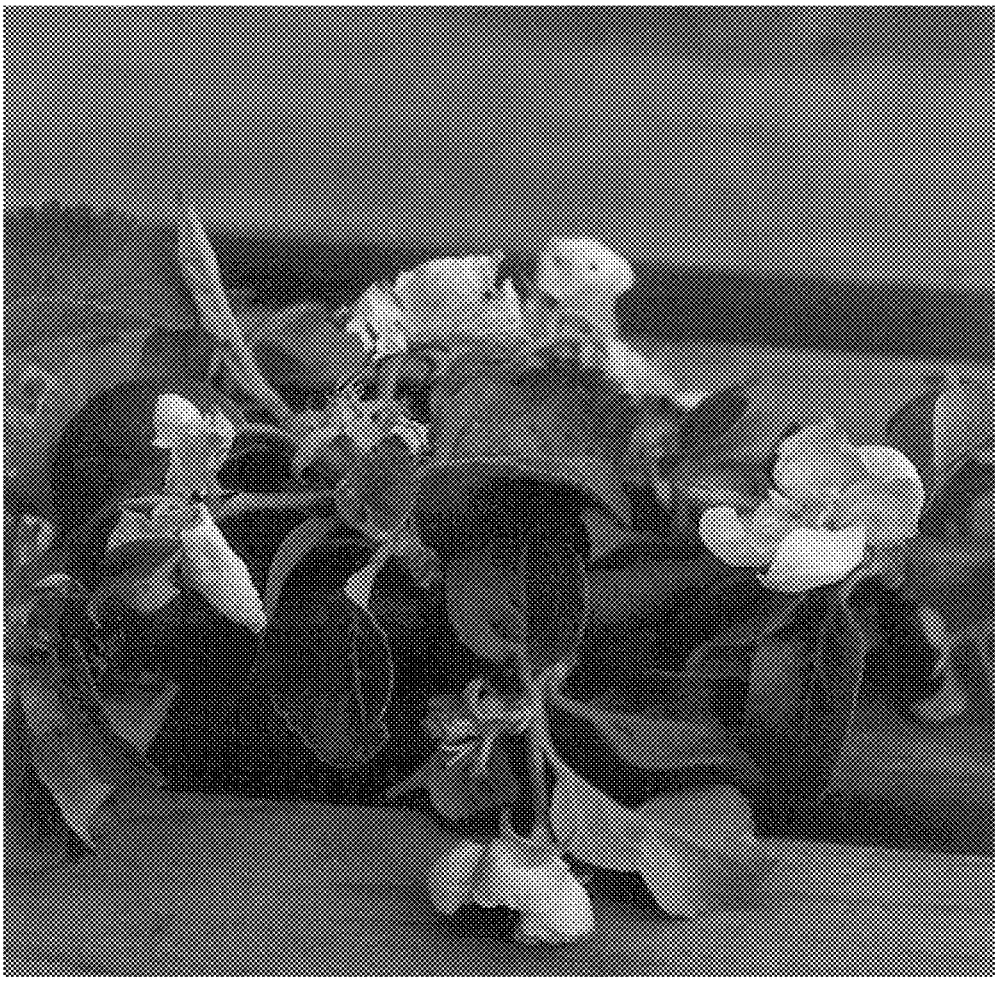
FIG. 5 is a view of a branch from the 'Pi 80 Select' variety that shows several blossoms.

Propagability. The performance of 'Pi 80 Select' with respect to layering was improved significantly by soil improvement using wood shavings. FIG. 4 shows a direct comparison of plants of the 'Pi 80 Select' variety and of the 'M 9' variety obtained by layering, and shows the difference in rooting of these plants. Table 1 shows a comparison of the performance of 'Pi 80' and 'Pi 80 Select' in stoolbed propagation by layering with 'M 9', 'M 4', and 'MM 106'.

TABLE 1

| Stoolbed performance of 'Pi 80' and 'P 80 Select' (2 sites, 5 years) | | | |
|---|---|---|---|
| Rootstock | Rooted layers for field no./year | % Rooted layers for field planting | Evaluation of rooting (1–5)* |
| Pi 80 normal propagation techniques | | | |
| Pi 80 | 2.5 | 56 | 2.2 |
| M 9 | 1.6 | 48 | 1.2 |
| M 4 | 2.9 | 51 | 1.4 |
| MM 106 | 3.8 | 72 | 2.3 |
| Pi 80 Select, soil improved with wood shavings | | | |
| Pi 80 Select | 15.0 | 78 | 3.2 |
| M 9 | 3.2 | 68 | 2.0 |
| M 4 | 14.2 | 56 | 2.7 |
| MM 106 | 8.4 | 71 | 2.7 |

*1 = no rooting, 5 = very good rooting

'Pi 80 Select' exhibits a better rooting system than 'Pi 80'. 'Pi 80 Select' has more root primordia under the bark than the 'Pi 80' variety. Observations are of virus free plants of both varieties and thus the better rooting capacity of 'Pi 80 Select' is not connected with the virus status of the plants.

Observations of 'Pi 80 Select' in McMinnville, Oreg. has also confirmed the rooting superiority of this variety. For example, under like growing conditions, the 'Pi 80 Select' variety has rooting which has been observed to be about four times better than 'M9'. This is consistent with the comparison between 'Pi 80 Select' and 'M9' set forth in the lower portion of Table 1 above. The comparision of 'Pi 80' to 'M9' set forth in the upper portion of Table 1 above shows that the 'Pi 80' is not nearly as strong a rooting plant.

In a specific comparison of plants showing under like growing conditions in stool beds in McMinnville, Oreg., the length of rootstocks in inches (averages of ten roots and three plants) was: 11.4 inches for 'Pi 80 Select', 7 inches for 'M 26' and 4.4 inches for 'M9' (337 clone). In addition, the number of rooting nodes per plant (averaged from ten plants) was: 11 nodes for 'Pi 80 Select', 5 nodes for 'M9' (337 clone) and 4 nodes for 'M26'. Again, the superior rooting capability of 'Pi 80 Select' is confirmed.

Observations of 'Pi 80 Select' plants growing in stool beds in McMinnville, Oreg. has indicated that the differences in rooting of the 'Pi 80 Select' variety is not a matter of juvenility. Contrary to what one would expect of a plant exhibiting juvenile characteristics, the observed 'Pi 80 Select' plants have few side shoots, lack spikes or spines, have a relatively short internode distance between buds, have rooting which improves as the 'Pi 80 Select' plants age, and have not been observed to exhibit suckering.

Growing Capacity and Yield. Table 2 shows the specific yield and growing capacity (crown volume as a percentage of 'M 26') of a variety of apple cultivars grafted as scions to 'Pi 80 Select', 'M 4', 'M 26' and 'MM 106' rootstock. Apple scions grown on 'Pi 80 Select' rootstock display similar growing capacity but higher specific yield than when grown on 'M 26' rootstock.

TABLE 2

| Yield and growing capacity of apple rootstocks | | | |
|---|---|---|---|
| | Specific yield | | |
| Rootstock | Crown Volume ($kg/m^3$) | % of M 26 | Crown volume % of M 26 |
| Cultivars 'Alkmene', 'Jonathan', 'Golden Delicious', 'Auralia' (3 sites, 8 years) | | | |
| Pi 80 Select | 3.4 | 103 | 96 |
| M 4 | 2.5 | 76 | 157 |
| M 26 | 3.3 | 100 | 100 |
| MM 106 | 2.9 | 88 | 145 |
| Cultivar 'Alkmene' (1 site, 11 years) | | | |
| Pi 80 Select | 6.1 | 127 | 103 |
| M 4 | 3.9 | 81 | 133 |
| M 26 | 4.8 | 100 | 100 |
| MM 106 | 5.6 | 117 | 148 |
| Cultivars 'Golden Delicious', 'James Grieve', 'Carola', 'Ontario' (2 sites, 11 years) | | | |
| Pi 80 Select | 3.9 | 105 | 90 |
| M 4 | 3.5 | 95 | 148 |
| M 26 | 3.7 | 100 | 100 |
| MM 106 | 4.0 | 108 | 139 |
| Cultivar 'Golden Delicious' (1 site, 12 years) | | | |
| Pi 80 Select | 6.6 | 129 | 102 |
| M 4 | 5.4 | 106 | 121 |
| M 26 | 5.1 | 100 | 100 |
| MM 106 | 6.3 | 123 | 108 |

Another measure of growing capacity of rootstocks is the man-hours required for pruning of cultivars. Table 3 shows expenditures for pruning 'Pi 80 Select', 'M 4', 'M 26', and 'MM 106' trees between the fourth and sixth years ('M 26'=100 percent).

Resistance to biotic damage. No problems were observed with scab, wooly aphids, and Phytophtora when 'Pi 80 Select' was grown in stoolbed and under orchard conditions. 'Pi 80 Select' is weakly susceptible to mildew and as susceptible to fireblight as 'M 26'. Suckers were very seldom observed as a source of dangerous infections in the orchard.

Table 4 shows resistance of 'Pi 80 Select' and other rootstocks to fire blight (1.0=susceptible, 9.0=highly resistant) in tests in which the rootstocks were artifically infected in greenhouses.

TABLE 3

| Relative man-hours required for pruning of cropping tree of between years 4 and 6 (M 26 = 100) | | | |
|---|---|---|---|
| Rootstock | Cuttings by saw (% of M 26) | Cuttings by scissors (% of M 26) | Cut wood kg/tree (% of M 26) |
| Pi 80 Select | 114 | 107 | 109 |
| M 4 | 196 | 145 | 217 |
| M 26 | 100 | 100 | 100 |
| MM 106 | 165 | 126 | 158 |

TABLE 4

| Rootstock | Resistance to fire blight* Resistance evaluation Test 1 | Test 2 | Test 3 |
|---|---|---|---|
| Pi 80 Select | 3.3 | 1.9 | 2.3 |
| M 4 | 3.8 | 1.5 | 6.9 |
| M 9 | 1.0 | 1.0 | 3.1 |
| M 11 | 1.0 | 1.3 | — |
| MM 106 | 2.2 | 2.4 | 4.4 |
| MM 111 | — | — | 6.6 |
| Budagovskij 9 | — | — | 2.6 |
| A 2 | — | — | 2.4 |
| M 26 | — | — | 2.3 |

*1.0 = susceptible, 9.0 = highly resistant.

Resistance to frost and freezing. Table 5 shows the results of a test program to evaluate the hardening, dehardening, and rehardening capacity of 'Pi 80 Select' and other rootstocks. 'Pi 80 Select' is not highly frost-resistant but has a good reaction ability, i.e., the physiological state can rapidly change as the temperature changes, especially as the temperature drops below freezing. By contrast, continental types have a poor reaction ability and die. 'Pi 80 Select' also has a good stability of hardening. In stoolbeds the rate of loss of 'Pi 80 Select' resulting from strong winters was low and no problems were encountered in orchards.

TABLE 5

| Rootstock | Winter frost resistance after artificial freezing* Hardening rate | Hardening intensity | Hardening stability | De-hardening | Re-hardening |
|---|---|---|---|---|---|
| Pi 80 Select | 7.4 | 5.8 | 7.4 | 6.9 | 7.6 |
| Supporter 1 | 8.8 | 5.0 | 5.3 | 3.2 | 8.5 |
| Supporter 2 | 7.2 | 5.4 | 7.2 | 7.2 | 7.0 |
| M 4 | 7.1 | 8.5 | 6.0 | 6.4 | 7.3 |
| M 9 | 5.2 | 6.0 | 7.1 | 6.8 | 6.1 |

*1.0 = very susceptible, 9.0 = very hard.

All trees of the new variety, insofar as I have been able to observe them, have been identical in all the characteristics described below. The description is of young trees on their own roots.

Propagation: Holds to distinguishing characteristics through succeeding propagation.

Parentage: Believed to be a mutation of 'Pi 80'.

Locality where grown and observed: Genbank Obst Dresden-Pillnitz at the Institut für Pflanzengenetik und Kulturpflanzenforschung Gatersleben, Germany and McMinnville, Oreg.

Tree:

*Size.*—Medium, like 'M26'.

*Vigor.*—Medium (see Table 1).

*Habit.*—Wide, rounded.

*Trunk.*—Smooth, not cracked (young trees).

*Branches.*—Wide angled, small group of dense branches in the crown.

*Bud.*—Bud color like R.H.S. 201D.

*Internodes.*—Medium (2–4 cm).

*Lenticels.*—Few (1–2 per cm), small to very small, light brown.

*Shoot.*—1 year shoot color like R.H.S. 148B, and 2 year shoot color like R.H.S. 195A.

*Leaves.*—Leaf stem: Leaf stem color like R.H.S. 144D. Size: Medium to large. Shape: Rounded. Color: Dark green to green, more specifically, upper leaf color like R.H.S. 137B and lower leaf color like R.H.S. 138B. Margin: Serrate. Petiole: Medium, straight.

Flowers:

*Diameter.*—One and one-half inches.

*Petals.*—Five.

*Color.*—Open bloom white with pink borders (like R.H.S. 155C). Closed bloom red-purple (like R.H.S. 62A).

*Sepal.*—Green (like R.H.S. 138B), pubescent.

*Pistil.*—Stigma: Bulbous on top.

*Anthers.*—13–15 single row. Pale yellow (like R.H.S. 9C).

*Fragrance.*—Very light.

*Bloom date.*—Approximately April 15 to April 23, when observed in the spring of the year 2000 in plants grown in a propagation bed at Weil Farms, Dundee Oreg.

Fruit of cultivars grafted onto 'Pi 80 Select' root stock:

*Skin coloration.*—Better than on 'M 26' or 'MM 106', similar to 'M 9': more red in the overcolor and/or more yellow as green in the ground color.

*Storability.*—Better than 'M 9' and 'M 26', similar to 'M 7'.

Compatibility: Excellent, better than 'M 26'.

Growing capacity: Similar to 'M 26', dependent on the cultivar.

Yield capacity: Better than 'M 26' and 'MM 106', lower than 'M 9'.

Anchorage: Better than 'M 9', similar to 'M 26'.

Resistance to biotic damage: Good resistance to winter frost, no problems with wooly aphids, crown gall and scab, weakly susceptible to mildew. Tolerant to *Phytophthora cactorium.*

I claim:

1. A new and distinct variety ('Pi 80 Select') of apple tree substantially as herein shown and described.

* * * * *